US011903806B2

(12) United States Patent
Dhar et al.

(10) Patent No.: US 11,903,806 B2
(45) Date of Patent: Feb. 20, 2024

(54) DEVICES AND SYSTEMS FOR TREATMENT OF URINARY INCONTINENCE, AND METHODS OF MAKING AND USING SAME

(71) Applicants: UNITED STATES GOVERNMENT AS REPRESENTED BY THE DEPARTMENT OF VETERANS AFFAIRS, Washington, DC (US); Wayne State University, Detroit, MI (US); Tino Toepper, Basel (CH); Bekim Osmani, Basel (CH); Bert Mueller, Basel (CH)

(72) Inventors: Nivedita Dhar, Bloomfield Hills, MI (US); Steven Majerus, Cleveland, OH (US); Jeremy Rickli, Royal Oak, MI (US); Tino Toepper, Basel (CH); Bekim Osmani, Basel (CH); Bert Mueller, Basel (CH)

(73) Assignees: United States Government As Represented By The Department Of Veterans Affairs, Washington, DC (US); Wayne State University, Detroit, MI (US); University of Basel, Basel (CH)

( * ) Notice: Subject to any disclaimer, the term of this patent is extended or adjusted under 35 U.S.C. 154(b) by 704 days.

(21) Appl. No.: 16/976,499

(22) PCT Filed: Mar. 1, 2019

(86) PCT No.: PCT/US2019/020318
§ 371 (c)(1),
(2) Date: Aug. 28, 2020

(87) PCT Pub. No.: WO2019/169277
PCT Pub. Date: Sep. 6, 2019

(65) Prior Publication Data
US 2020/0405467 A1    Dec. 31, 2020

Related U.S. Application Data

(60) Provisional application No. 62/637,707, filed on Mar. 2, 2018.

(51) Int. Cl.
*A61B 5/20*  (2006.01)
*A61F 2/00*  (2006.01)
(Continued)

(52) U.S. Cl.
CPC ............ *A61F 2/004* (2013.01); *A61B 5/0022* (2013.01); *A61B 5/205* (2013.01); *G16H 40/67* (2018.01);
(Continued)

(58) Field of Classification Search
CPC ... A61F 2/004; A61F 2250/0004; A61B 5/205
See application file for complete search history.

(56) References Cited

U.S. PATENT DOCUMENTS 6,135,945 A     10/2000  Sultan
2003/0191504 A1* 10/2003 Meadows .......... A61N 1/36071
                                                        607/33
(Continued)

FOREIGN PATENT DOCUMENTS

WO    WO 2004/037082 A1    5/2004

*Primary Examiner* — Kaylee R Wilson
(74) *Attorney, Agent, or Firm* — Ballard Spahr LLP

(57) ABSTRACT

An artificial urinary sphincter can include a cuff configured to surround a portion of a length of a urethra. An actuator is configured to selectively apply a force to the cuff to thereby apply variable amount of pressure to the urethra. A controller is configured to adjust the application of the force by the actuator to cause the cuff to apply the variable amount of pressure to the urethra. A sensor can be in communication
(Continued)

with the controller and configured to detect pressure applied against the cuff by the urethra. The controller is configured to cause the cuff to apply a first closing pressure to the urethra. In response to a detection of a threshold pressure increase by the sensor, the controller is configured to cause the cuff to apply a second closing pressure that is greater than the first closing pressure and that prevents urine from exiting the urethra.

17 Claims, 5 Drawing Sheets

(51) Int. Cl.
  *G16H 40/67* (2018.01)
  *A61B 5/00* (2006.01)
(52) U.S. Cl.
  CPC ............ *A61F 2250/0002* (2013.01); *A61F 2250/0004* (2013.01)

(56) References Cited

U.S. PATENT DOCUMENTS

| | | |
|---|---|---|
| 2004/0172087 A1 | 9/2004 | Forsell |
| 2005/0240144 A1 | 10/2005 | Wassemann et al. |
| 2006/0056161 A1* | 3/2006 | Shin ............... G01L 19/146 361/783 |
| 2009/0259093 A1 | 10/2009 | Bhat |
| 2012/0157759 A1 | 6/2012 | Wirbisky et al. |
| 2012/0253165 A1* | 10/2012 | Yen ............... A61B 3/16 600/398 |
| 2014/0039242 A1* | 2/2014 | Domel ............ A61F 2/004 600/30 |
| 2015/0165141 A1* | 6/2015 | Sauvageot ....... A61M 16/1075 600/407 |
| 2015/0202034 A1 | 7/2015 | Seebach et al. |
| 2015/0374288 A1 | 12/2015 | Uromens et al. |

* cited by examiner

DEVICES AND SYSTEMS FOR TREATMENT OF URINARY INCONTINENCE, AND METHODS OF MAKING AND USING SAME

CROSS-REFERENCE TO RELATED APPLICATIONS

This application is a national stage filing under 35 U.S.C. § 371 of International Application No. PCT/US2019/020318, filed on Mar. 1, 2019, which claims priority to and the benefit of the filing date of Provisional Application No. 62/637,707, filed on Mar. 2, 2018. These applications are hereby incorporated by reference herein in their entireties.

BACKGROUND

Normal micturition requires the coordination of a neuronal circuit between the brain and spinal cord and the bladder and urethra. Neurogenic stress urinary incontinence (NSUI or SUI), defined as urinary incontinence that occurs on exertion, effort, sneezing, or coughing, is common in spinal cord injury (SCI) patients with lower motor neuron lesions involving the conus medullaris, cauda equina or peripheral pelvic nerves. This classically occurs in sacral spinal cord and/or pelvic injuries; these individual/combined injuries often develop in military conflicts, civil disasters, and domestic traumatic situations associated with improvised explosive devices (IED). Malfunction of the pudendal nerve in these patients, which innervates the external sphincter, results in an open fixed bladder neck and prevents reflex contraction of the striated sphincteric fibers during stress, leading to NSUI. Associated malfunction of pelvic nerves that innervate the detrusor muscle can lead to detrusor underactivity.

The treatment of NSUI remains a therapeutic challenge. Stress urinary incontinence (SUI) is a major ubiquitous health problem that affects female patients, male patients after prostate surgery, and children with incompetent bladder outlets. The fear of lack of control and the embarrassment associated with involuntary loss of urine often causes significant changes to patient behaviors as the patients struggle to cope. SUI remains a debilitating condition that adversely impacts all domains of quality of life, and is associated with significant social stigma and health economic burden.

SUI is a prevalent condition that interferes with aging female patients' health-related quality of life. Age and obesity are major risk factors to the development of female SUI, a concern given the current population age demographic shift and increase in obesity. There are non-surgical treatments available, including pelvic floor muscle training, electrical stimulation, and urethral inserts; although when these measures result in inadequate resolution or are not tolerated, surgical correction becomes a viable option.

SUI has also become common in male patients due to an increase in the number of radical prostatectomies (RP) performed annually. Approximately one of every two male patients who undergoes a RP suffers from post prostatectomy SUI. Early and mild degrees of SUI after prostate surgery may be improved by intensive pelvic floor muscle training and life style modifications, but when conservative therapy options fail, surgical treatment is recommended.

With respect to children, an incompetent bladder outlet is often present in complex pediatric urologic patients. This results from either anatomical anomalies (bladder exstrophy-epispadias complex) or from sphincter incompetence as with neurogenic bladder dysfunction (myelimenogocele, spinal cord injury, tethered cord, sacral agenesis and transverse myelitis). The social stigma of persistent wetting is a common problem faced by such children and can lead to self-esteem issues, shame, isolation, poor school performance, aggressiveness, and other behavioral changes. These patients usually require bladder neck surgery to achieve continence, but outcomes are often poor. Alternative treatments such as slings and urethral bulking agents have proven ineffective in such children and the artificial urinary sphincter (AUS) is the only device capable of achieving continence and possibly avoiding surgical creation of catheterizable channels with its obligate bowel resection. However, there is currently no FDA approved AUS for pediatric patients in the USA. The FDA definition of "pediatric", for purposes of device development, encompasses devices used for patients who are 21 years of age or younger at the time of diagnosis or treatment. For children with a history of prior failed attempts at bladder neck reconstruction, the only surgical option for continence at this time is bladder neck ligation. Conventional alternatives for urinary incontinence are unavailable for children. Thus, there is a need for a more effective UI solution.

Therapeutic options for SCI patients can differ from treatment strategies in patients with stress urinary incontinence (SUI) without neurogenic lesion. Due to the neurogenic pelvic floor dysfunction, active conservative measures, such as pelvic floor exercises or biofeedback, are virtually impossible in the majority of patients. The success of external electrostimulation or duloxetine treatment on NSUI in patients with SCI has not yet been assessed, but seems to be limited due to the above-mentioned reasons. Thus, surgical procedures are the most frequently used treatment options in SCI patients.

Surgical Options: Procedures to treat sphincter incompetence are suitable only when the detrusor activity is, or can be, controlled. Several surgical options exist, including urethral bulking agents, periurethral balloons, fascial and synthetic slings as well as artificial urinary sphincters (AUS). However, many surgical treatment options for SUI are also difficult to apply to SCI patients. The efficacy of urethral bulking agents to improve urethral mucosal coaptation in an effort to limit stress-induced leakage is modest at best, repeat injections are the norm, and long-term follow-up is conspicuously lacking. Periurethral balloons show an acceptable success rate at mid-term follow-up in non-neurogenic patients, but are associated with such a high rate of complications and reoperations that this option should only be considered as a last-resort technique.

Female Slings: The goal of a sling procedure in patients with NSUI is to induce increased outlet resistance so that the patient can be managed with intermittent catheterization (IC), a common and acceptable method of bladder emptying in SCI patients. Over the last decade, non-absorbable mesh became the material of choice for slings. However, in 2008 and 2011 the FDA warned of potentially serious complications with transvaginal mesh implants in response to a growing number of reported complications related to mesh erosion, infection, bleeding, pain during sexual intercourse, organ perforation, and urinary problems. This has resulted in an increased caution among female patients considering mesh slings and a search for new, safer procedures among physicians and the industry. A mesh sling, intentionally placed under enough tension to induce increased outlet resistance so that the patient can be managed with IC, heightens the already significant risk of mesh erosion and associated complications. Continence rates with the autologous rectal fascia bladder neck sling in female SCI patients ranges between 70-88%. While this sling does not consist of synthetic material, making infection and erosion less likely than with mesh slings, its long-term durability is unknown. This is an important consideration, particularly for young women, in whom this procedure may have to last for decades. Potential additional disadvantages to consider include graft harvest morbidity, harvest site incision size, inconsistent graft strength, poor graft quality and graft unavailability.

Male Slings: Male incontinence slings are newer interventions for male SUI. They are minimally invasive, more economical, with lower risk for infection and fewer complications than an AUS. Slings are an option for some men with mild to moderate SUI but are not good options for those with moderate to severe SUI. They are suboptimal in SCI male patients with SUI either due to increased risk of complications or significantly decreased efficacy in terms of continence. In general, possible sling complications include urinary retention, persistent pain and infection.

Artificial Urinary Sphincter: The International Consultation on Incontinence classifies the Artificial Urinary Sphincter (AUS) with a Grade A recommendation for the treatment for NSUI. See Abrams P, Cardozo L, Fall M, et al. The standardisation of terminology of lower urinary tract function: Report from the Standardisation Sub-committee of the International Continence Society. *Neurourol Urodyn* 2002; 21:167-78. The AMS 800 (Boston Scientific) is considered the gold standard of NSUI surgical management for men, and is the only approved AUS device in the USA. The AMS 800, while providing excellent continence rates, has limited utility in SCI patients due to a high urethral cuff erosion rate (18%) and frequent incidence of device malfunction (45%). SCI patients undergoing AMS 800 implantation have a higher number of device malfunctions, sphincter replacements and urethral erosions compared to patients with SUI of non-neurogenic etiology. In summary, high continence rates can be achieved, but the complication and revision rates of the AMS 800 in SCI patients are substantial enough that it is becoming an abandoned treatment modality. Decision-making in the surgical treatment for male SCI patients with NSUI is challenging because few valuable options exist.

The AMS 800 is not FDA approved for women, therefore, experience of implanting the AUS in women remains limited worldwide. Data are scarce regarding the long-term functional results and mechanical survival of the AUS in female SCI, which is unfortunate since the AUS is the preferred treatment for patients with NSUI. SCI female patients with NSUI have become a desperate population with no safe and effective solution to manage their leakage.

Accordingly, a need exists for a better alternative solution for both male and female patients suffering from NSUI.

SUMMARY

Disclosed herein, in one aspect, is a smart artificial urinary sphincter device.

An artificial urinary sphincter can comprise a cuff configured to surround a portion of a length of a urethra and an actuator in communication with the cuff and configured to selectively apply a force to the cuff to thereby apply a variable amount of pressure to the urethra. A controller can be in electrical communication with the actuator and configured to adjust the application of the force by the actuator to cause the cuff to apply the variable amount of pressure to the urethra. At least one sensor can be in communication with the controller. The sensor can be configured to detect pressure applied against the cuff by the urethra. The controller can be configured to cause the cuff to apply a first closing pressure to the urethra. In response to a detection of a threshold pressure increase by the sensor, the controller can be configured to cause the cuff to apply a second closing pressure that is greater than the first closing pressure and that prevents urine from exiting the urethra.

The at least one sensor can be a dielectric elastomer transducer.

The at least one sensor can comprise a plurality of metal electrodes embedded in an elastic elastomer membrane.

The at least one sensor can have a response time below 20 milliseconds in response to pressure changes.

The at least one sensor can be configured to change capacitance in response to mechanical deformation, and wherein the controller is configured to detect a change in capacitance to the sensor.

The actuator can be configured to move the cuff from an open position to a closed position.

At least a portion of the artificial urinary sphincter can be configured to be installed in a pelvic cavity of a user.

The actuator can be an electric actuator.

The actuator can be a linear actuator.

Upon a detected condition, the controller can be configured to cause the actuator reduce the pressure to the cuff to thereby move the actuator to the open position.

The artificial urinary sphincter can further comprise a wireless receiver in communication with the controller. The wireless receiver can be configured to receive a release signal, wherein the detected condition is a receipt of the release signal.

The detected condition can be a sensed pressure from the at least one sensor that is greater than a threshold value and that is maintained for a threshold amount of time.

The artificial urinary sphincter can comprise a battery that is configured to be charged wirelessly.

The artificial urinary sphincter can comprise a charge receiver that is configured to be implanted between 2 and 3 cm below the skin of a user.

The first closing pressure can be between 50 and 70 mmHg.

The second closing pressure can be about 200 mmHg.

A method can comprise implanting the artificial urinary sphincter as in any of claims 1-14 in a patient, detecting, using the sensor, a pressure measurement above the threshold pressure, and, in response to receiving the pressure measurement above the threshold pressure, providing a signal to the actuator to cause the cuff to apply the second closing pressure.

BRIEF DESCRIPTION OF THE DRAWINGS

FIG. 2A depicts system activation as a result of either user request or extraneous sphincter pressure sensed by the cuff. FIG. 2B depicts exemplary implant control electronics, including a cuff actuator and a sensor-enabled urethral cuff.

DETAILED DESCRIPTION

Figure 1A:
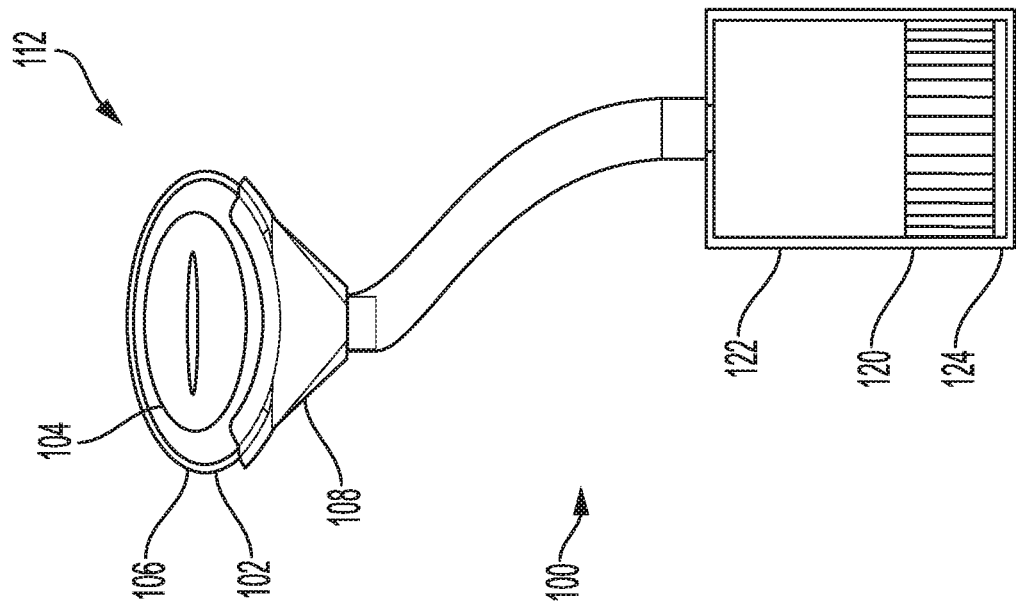
FIGS. 1A and 1B depict an exemplary Smart Artificial Urinary Sphincter (SAUS) device as disclosed herein, with the cuff in open (FIG. 1A) and closed (FIG. 1B) configurations.
Figure 1B:
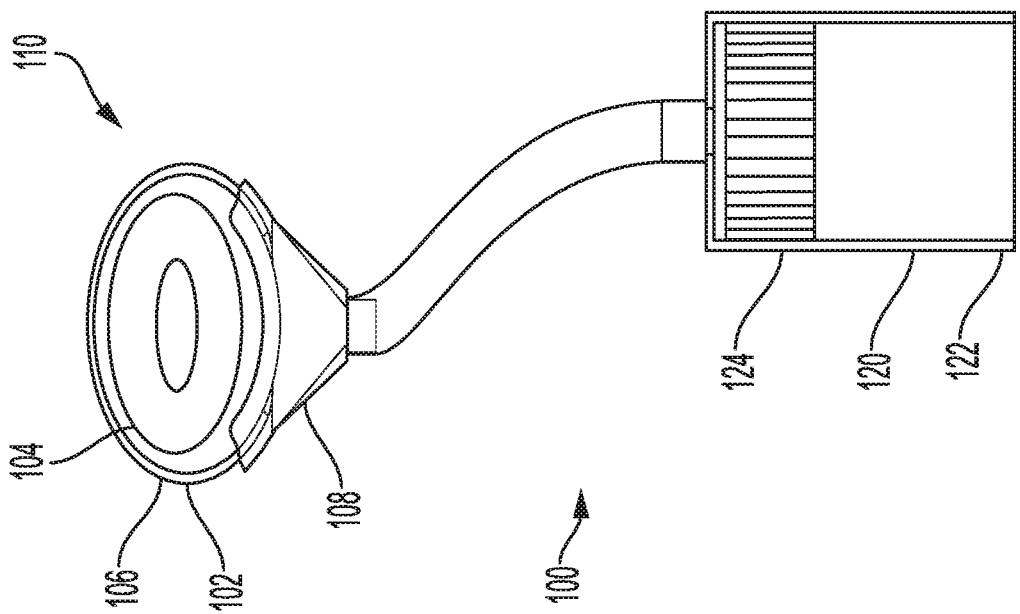

The present disclosure can be understood more readily by reference to the following detailed description, which includes examples, drawings, and claims. However, before the present devices, systems, and/or methods are disclosed and described, it is to be understood that this disclosure is not limited to the specific devices, systems, and/or methods disclosed unless otherwise specified, as such can, of course, vary. It is also to be understood that the terminology used herein is for the purpose of describing particular aspects only and is not intended to be limiting.

The following description is provided as an enabling teaching of the disclosed invention in its best, currently known embodiment. To this end, those skilled in the relevant art will recognize and appreciate that many changes can be made to the various aspects of the disclosure, while still obtaining the beneficial results of the disclosure. It will also be apparent that some of the desired benefits of the disclosure can be obtained by selecting some of the features of the disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

As used throughout, the singular forms "a," "an" and "the" include plural referents unless the context clearly dictates otherwise. Thus, for example, reference to "a sensor" can include two or more such sensors unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Optionally, in some aspects, when values are approximated by use of the antecedents "about," "substantially," or "generally," it is contemplated that values within up to 15%, up to 10%, or up to 5% (above or below) of the particularly stated value or characteristic can be included within the scope of those aspects.

As used herein, the terms "optional" or "optionally" mean that the subsequently described event or circumstance may or may not occur, and that the description includes instances where said event or circumstance occurs and instances where it does not.

Disclosed herein, in various aspects and with reference to FIGS. 1A-2B, is a device for treating urinary continence that will be referred to herein as the "Smart Artificial Urinary Sphincter" or "SAUS" device. A healthy sphincter provides a dynamic range of pressures, depending on the circumstances, to prevent leakage. Thus, continence is not simply a function of two states (closed and open) but a rapid, dynamic response to sudden pressure changes caused by actions such as coughing. In contrast, the state of the art artificial urinary sphincter, AMS 800, introduced in 1983, generates only closed and open states. Since 1983, the basic design has been largely unchanged. This device consists of an inflatable occluding cuff, a pressure regulating balloon and a control pump. The AMS 800 is a fluid-driven mechanical system that is manually operated by the patients, thereby requiring fine motor skills and force generation. While AMS 800 can be safe and effective, there are limitations such as the requirement for manual dexterity to operate the device, a static high urethral cuff pressure, a pre-set geometry in the cuff diameter and the inability to alter the cuff pressure and to correct for delayed tissue atrophy without further surgery. Further, AMS 800 has revision and explantation rates of up to 55% due to mechanical failure, fluid leaks, urethral atrophy, infection, and cuff erosion.

It is contemplated that momentary increases of cuff pressure can be critical to prevent incontinence caused by sudden increases in intra-abdominal pressure such as with coughing and positional changes. The existing AMS 800's resting cuff pressure is set at a level high enough to prevent leakages due to coughing and positional changes, however, these high resting pressure levels lead to increased rates of urethral atrophy/erosion, infection and resurgence of incontinence. As further described herein, decreasing atrophy/erosion and infection rates requires a lower resting cuff pressure during normal operation and initiation of higher cuff pressure levels only during coughing, positional changes, and the like. The smart cuff of the SAUS device can sense these pressure changes using a sensor (e.g., a DET sensor) attached to the cuff exterior. Sensor responses (e.g., DET sensor responses) can then be used to signal for momentary increases in cuff pressure to prevent urinary leakage.

Embodiments of the SAUS device, as disclosed herein, can apply and maintain a first closing pressure on the urethra via a cuff during normal conditions. For example, the first closing pressure can be between 50 and 70 mmHg. The first closing pressure can be sufficient to overcome the pressure in the bladder to prevent urine from exiting the urethra under normal conditions, such as, for example, when a user is resting. In situations where the bladder pressure increases, for example, if a user coughs, sneezes, or exerts himself/herself during physical activity, the pressure in the bladder can increase above the threshold necessary to force urine past the cuff when the cuff is applying the first closing pressure. Under these conditions, the SAUS device can be configured to detect an increase in the bladder pressure. The SAUS device can further be configured to increase the pressure applied to the urethra to a second closing pressure that is greater than the first closing pressure to thereby prevent urine from exiting the urethra when the bladder pressure is elevated. The SAUS device can further detect a decrease in bladder pressure and, in response, decrease the amount of pressure on the urethra. Accordingly, the SAUS device can mimic the natural urinary sphincter by incorporating sensory feedback and a sufficiently fast actuator to respond to sudden pressure changes. As further disclosed herein and summarized in Table 1, the SAUS device can provide significant advantages that are not achievable with current alternative devices and systems, such as the state-of-the-art AMS 800 device.

TABLE 1

| Comparison of AMS 800 and SAUS Device | |
|---|---|
| Exemplary SAUS Device | AMS 800 |
| Dynamic urethral cuff pressure | Static, high urethral cuff pressure |

TABLE 1-continued

Comparison of AMS 800 and SAUS Device

| Exemplary SAUS Device | AMS 800 |
|---|---|
| Smart pressure sensing cuff | No pressure sensing capability |
| Millisecond closed loop pressure feedback | No closed loop pressure feedback |
| Low resting urethral cuff pressure | High resting urethral cuff pressure |
| No hydraulic systems | Hydraulic driven system - 20% fluid leaks |
| Simple surgical implantation | Complex surgical implantation |
| Patient one-touch remote control for void/close | Patient manual pump control to void/close |
| Gender and disease-specific cuff control capabilities | No adaptive cuff control capabilities |
| Does not require fine motor skills and force generation | Requires fine motor skills and force generation |
| No component in scrotum | Scrotal pump |
| Treatment option for men and women | Not FDA approved for women |
| Externally rechargeable implanted battery | Mechanical activation |
| Data collection accessible to physician | No data collection |

According to various embodiments, a SAUS device 100 can include a cuff 102 that is sized and otherwise configured to surround a portion of a length of a urethra 104. The cuff 102 can comprise a band 106 that is retractable and protractable (configured for advancement) into and out of, respectively, a band housing 108 in order to move the cuff 102 from an open position 110 to a closed position 112. The band housing 108 can comprise a generally Y-shaped body having an interior path through which the band 106 can extend. The band housing 108 can cooperate with the band 106 to define the portion of the cuff 102 that engages the urethra 104. When the cuff is in the open position 110, urine can pass through the urethra, while in the closed position 112, urine is inhibited from passing through the urethra. In some embodiments, the cuff can have dimensions of 10-30 mm long, or 15-25 mm long, or 20 mm long (along the length of the urethra) by 20-50 mm or 25-35 mm in circumference.

The band 106 and, accordingly, the cuff 102 can be actuated to move about and between the opened and closed positions 110, 112 via an actuator 120. According to some aspects, the actuator can be a linear actuator comprising a housing 122 and a shaft 124 that is movable within the housing 126 along an axis. Each end of the band 106 can couple to the actuator shaft 124, so that, as the shaft of the actuator retracts, the shaft pulls the band to thereby apply pressure to the urethra. In further embodiments, a first end of the band 106 can couple to the actuator shaft 124, and the second end can couple to the housing 108 so that as the actuator shaft 124 is retracted, the band applies pressure to the urethra. According to further aspects, the actuator can be a rotary actuator. The rotary actuator can turn a spool that retracts one or both ends of the band to thereby cause the band to apply pressure to the urethra. Although not preferred in some embodiments, it is contemplated that hydraulic actuators can be used. For example, a hydraulic actuator can actuate an inflatable bladder that applies pressure to the urethra to thereby close the urethra and prevent urine from passing therethrough. In some embodiments, the inflatable bladder can surround the urethra.

According to some aspects, the actuator 120 can provide 10 mm or more of travel for the cuff system, a cuff closing force of 3-5 N, and speeds greater than 250 mm/s. In exemplary non-limiting aspects, it is contemplated that the actuator system can comprise one or more of a Faulhaber Linear DC-Servomotor (Series LM 0830 015-01), Faulhaber Stepper Motors (FDM0620-ww-ee V2, rotary motor), a Physik Instrumente V-273 PIMag Voice Coil Linear Actuator, or an Electro Mechanisms Inc. T30 tubular solenoid. More generally, it is contemplated that the actuator system can comprise one or more actuation technologies, including, for example and without limitation, DC-servomotors, stepper motors, linear/rotary solenoids, and the like. In exemplary aspects, it is contemplated that the actuator for the SAUS device can meet various requirements, including, for example and without limitation, low power, implantable, high speed (250 mm/s), 3-5 N, and a minimum of 10 mm stroke. In further aspects, it is contemplated that other actuation methods such as a distance-multiplying linkage, push-pull actuation, or a normally-closed topology can be used to minimize cuff closure time.

In additional aspects and as further disclosed herein, the SAUS device can be controlled by SAUS implant electronics 190, which can optionally comprise an integrated microcontroller 192 that can control an amount of pressure that the cuff applies to the patient's urethra. The controller can allow patient-specific cuff control algorithms that satisfy a specific patient or class of patient incontinence requirements. According to some embodiments, resting hold pressure can be set at 50-70 mmHg and close pressure can be set between 180-220 mmHg, and optionally 200 mmHg. In further embodiments, the close pressure can be varied according to a pressure measurement at the cuff in order to maintain a close pressure that is higher than the pressure that the urethra applies to the cuff.

The SAUS device 100 can further include a sensor 140 that is configured to detect pressure applied against the cuff by the urethra. In some embodiments, a plurality of sensors 140 can be used to detect pressure applied against the cuff by the urethra. Optionally, the sensor(s) 140 can comprise one or more low-voltage dielectric elastomer transducers (DETs). That is, each sensor 140 can comprise one DET or a plurality of DETs. In some embodiments, the sensor 140 can comprise an array of DETs. Each of the DET's thickness can be on the order of nanometers and, in some embodiments, about 85 nm thick. The array can optionally have a density of 0.1 transducers per $mm^2$ to the actual geometry of the SAUS cuff implant. However, it is contemplated that other densities can be used. It is contemplated that such DETs can exhibit a strain-stress behavior comparable to human tissues and efficiently convert electrical energy into mechanical energy. As further discussed herein, it is contemplated that molecular beam deposition (MBD) can allow for fabricating elastomer layers several hundred nanometers thin and that the obtained nanostructures can generate 6% strain by applying voltages as low as 12 V. It is further contemplated that such nanometer-thin DETs can be fabricated on flexible substrates or even directly on medical implants without creating further geometrical restrictions. In exemplary aspects, the sensors can comprise metal electrodes embedding an elastic elastomer membrane. In further aspects, it is contemplated that pre-stretched electrodes can be used to keep the DET structures as soft as the elastomer and avoid stiffening by the gold. In additional aspects, it is contemplated that the DET can be reliably fabricated using biocompatible nanostructures. Optionally, in further aspects, the DET sensor without microelectronics can exhibit response times below 20 ms to pressure changes. In still further aspects, the multi-layered DETs can remain operational even if some layers fail due to breakdowns, demonstrating the phenomena of so-called "self-clearing." Although specifically described as comprising DETs, it is contemplated that other types of pressure sensors can be used to detect pressure applied against the cuff.

The sensor 140 can be attached to, or integrated into, the cuff 102. In the case of a DET sensor, when the DET structure is mechanically deformed, its capacitance can change and create an electrical signal that can be provided to the controller. In turn, the controller can cause the actuator to change the cuff pressure. This closed loop feedback mechanism (e.g., millisecond closed loop feedback mechanism) can permit the SAUS device cuff to rest at a lower baseline pressure on the urethra. Observed responses from the sensor-enabled cuff can provide feedback to the microcontroller to adjust the actuator position for higher or lower cuff pressure and, thereby, urethral outflow resistance. By keeping the resting urethral cuff pressure low, the incidence of urethral erosion and associated complications can be reduced compared to the AMS 800.

In exemplary aspects, a battery 160 can power the microsystem and actuator. Optionally, in these aspects, the battery 160 can be the EaglePicher Contego 325 mAh Battery, which has been used in medical implantable devices and is in compliance with ISO 13485 and ISO 9001. In further aspects, the battery can have a nominal voltage of 3.6 V, a weight of 40 g, and a volume of approximately 7 cm$^3$. It is contemplated that the battery can be recharged by a transcutaneous energy transfer (TET) system as is known in the art. Because portions of the SAUS device can be implanted just beneath the patient's skin, wireless recharging can be feasible using typical inductive charging methods. In use, it is contemplated that the SAUS device can be within 1-2 cm of the skin surface to enable efficient wireless operation with weekly charging to occur while the patient is resting. In further embodiments, the SAUS device can comprise an energy harvester (e.g., thermal or mechanical) that can be configured to provide power to the SAUS device.

One advantage of the SAUS device is that it can be capable of adapting the urethral cuff pressure, thereby significantly improving continence and minimizing urethral damage. It is further contemplated that patients using the SAUS device can have a remote control to open and close the cuff, thereby allowing patients with limited manual dexterity to operate the SAUS without mechanical effort or assistance. That is, the SAUS device 100 can comprise a wireless transceiver 194 that can receive signals from a wireless remote to cause the cuff to release pressure on the urethra to thereby allow urine to flow therethrough. According to various aspects, the controller can further comprise a manual shutoff that, when pressed, causes the cuff to apply a maximum shutoff pressure to prevent leakage. It is still further contemplated that the SAUS device 100 can be configured to, upon detecting a threshold pressure against the cuff, release pressure on the urethra and open the cuff to allow urine to flow therethrough. In this way, the SAUS device can prevent damage to the patient user from excessive pressure, for example, due to an over-full bladder.

In some embodiments, the sensor 140 can determine a rate of pressure change, and the SAUS device 100 can close the cuff in response to detecting a rate of pressure change that is above a threshold. For example, when the pressure applied against the cuff, which is sensed by the sensor 140, changes by a rate above the threshold, the controller can cause the cuff to close. In some embodiments, the controller can cause the cuff to apply a select pressure to the urethra, wherein the select pressure is a function of both a pressure measurement and measurement of the rate of pressure change.

Figure 2A:
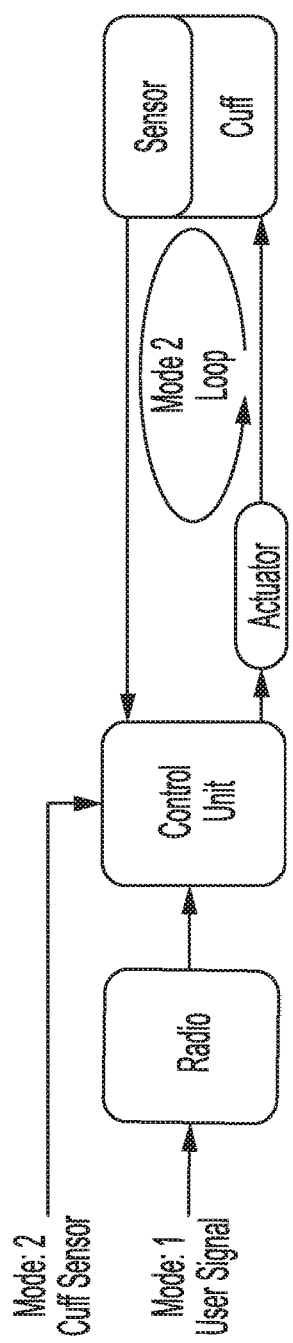
FIGS. 2A-2B are schematic diagrams depicting exemplary control logic for a SAUS device as disclosed herein.

Accordingly, the SAUS device 100 can be configured to operate under two different control schemes: (1) user controlled release of the SAUS cuff pressure and (2) closed loop feedback to dynamically control the SAUS cuff pressure, as shown in FIG. 2A.

In still further aspects, the SAUS device can be completely implantable in the human body. Another advantage of the SAUS device is that it can operate with a gender and disease-specific control algorithm capable of self-adaptation to the patient's urethral morphology. It is contemplated that the SAUS device can be implanted in a user's pelvic cavity. Accordingly, the SAUS device can be a treatment option for both males and females, unlike the AMS 800 that requires placement in the scrotum. Further, because the SAUS device can be implanted in the pelvic cavity, during use of the SAUS device, wheel chair-bound users will not constantly be sitting on their device which often results in extrusion of the device from the scrotum. Since the SAUS has a simpler geometry, it is contemplated that the SAUS device can be easier to surgically implant and cost less to produce than the AMS 800.

Yet another advantage of the SAUS device is that by employing an electrically actuated actuator as disclosed herein, the SAUS device can eliminate the hydraulic component of the AMS 800, which results in fluid leaks that require surgical revision in up to 20% of patients.

In use, it is contemplated that the SAUS device can be configured to increase cuff pressure on the urethra in response to increased pressure in a response time that is less than 30 milliseconds. This response time can be a combination of pressure change detection time (from sensor 140), processing time, signal transfer time, and actuator movement time.

Optionally, determination of the threshold can be based on the baseline behavior and variation of the cuff sensor response during normal patient activity. Activation and hysteresis thresholds can be continuously calculated based on a window that is significantly longer than typical detrusor contractions. In this way, the SAUS device 100 can determine an ideal first pressure. Moreover, the wavelet transform can enable the SAUS device 100 to adapt to changes in the sensor over time. Optionally, the SAUS device 100 can implement multi-resolution analysis using wavelet transform to enhance control accuracy depending on the variance of DET (or other pressure sensor) signals. Threshold detection software can run in real-time on the implanted microcontroller; therefore, given the hardware limits of a wireless microsystem, it is contemplated that the SAUS device can provide a balance between the threshold detection complexity and response time and power consumption.

The SAUS implant can be encapsulated in biocompatible polymers. These polymers include, for example and without limitation, Parylene-C, nontoxic epoxy resin, silicone gels, silicone elastomers, and the like. It is contemplated that the packaging can be applied via micro-molding and chemical vapor deposition as is known in the art.

Sensor Electrodes and Methods and Systems for Production Thereof

In exemplary aspects, the sensor 140 can comprise at least one electrode. The electrode can comprise a stretchable substrate, such as, for example, polydimethylsiloxane (PDMS). One PDMS formula can include DOW CORNING SYLGARD 184 silicone elastomer and OS-20 silicone fluid. The PDMS can be manufactured at a ratio of 10:1:10 of elastomer to curing agent to solvent agent on polystyrene films. The substrate can be cured at a temperature of 70 degrees Celsius for twenty-four hours. The membrane can be stabilized during deposition by mounting them to silicone substrates at a distance of 450 mm from a crucible and a UV lamp. UV cross linking of thiol-terminated polydimethylsiloxane (SH-PDMS) can be initiated in situ and/or by subsequent irradiation from an externally mounted source (e.g., an $H_2D_2$ L11798 light source) through a $CaF_2$ window. The wavelength spectrum of the deuterium lamp can range from 160 to 450 nm with a peak intensity at a wavelength of 190 nm.

Materials can be evaporated thermally under ultra-high vacuum (UHV) conditions at a base pressure of $10^{-7}$ mbar. Synthesized SH-PDMS can be evaporated using low-temperature effusion cells with a two $cm^3$ crucible. The material can be evaporated at a crucible temperature of 140° C., well below the thermal degradation temperature of vinyl and thiol end groups and corresponding to a deposition rate of about 30 nm/hr.

The growth of the metal and elastomer films can be controlled on line using a SE801 spectroscopic ellipsometer and cross-checked after deposition via atomic microscopy surface scans along intentionally induced scratches. To examine in situ the optical properties of the forming nanostructures, SpectraRay3 software can be utilized. Spectroscopic $\Psi$- and $\Delta$-values in the range 190 to 1050 nm can be monitored at a frequency between 0.5 to 2 Hz at an incident angle of 70° to the normal of the substrate surface. The 4 mm wide incident beam can result in a 4×10 $mm^2$ spot area on the substrate.

Electrodes can be prepared by thermally evaporating gold and chromium in the UHV system at a residual pressure of $10^{-7}$ mbar. Two high-temperature effusion cells with 10 $cm^3$ PBN crucibles can be used as molecular beam sources. The evaporation temperatures for gold and chromium can be 1,400° C. and 1,440° C., which can correspond to a deposition rate of about $1.1*10^{-2}$ nm/s and $0.3*10^{-2}$ nm/s, respectively. The substrate can be mounted at a distance of 450 mm from the crucibles.

In one embodiment, an electrode can be manufactured according to the following method. A PDMS substrate can be UV-treated as disclosed herein to improve wetting for a SH-PDMS layer. A layer of SH-PDMS (e.g., 50 nm) can be deposited via molecular beam deposition (MBD) while simultaneously curing in situ with UV irradiation. Subsequently, a layer of SH-PDMS (e.g., 10 nm) can be deposited via MBD without UV curing. Next, a layer of gold (Au) (e.g., 25 nm) can be deposited thereon form covalent bonds with the thiol groups to the PDMS chains, which can subsequently be crosslinked via UV irradiation for one hour.

Optionally, the resulting electrode can undergo strains of at least 60% without failure. That is, the electrode can remain conductive for a strain of up to 60%. The elastic modulus of the electrode can be 12+/−9 MPa. It should be understood that lower doses of irradiation can result in lower elastic moduli. Optionally, the electrode's resistivity can increase by 50% when the electrode undergoes a strain of 60%. The change in resistivity can be approximately characterized as a linear relationship with respect to strain. In further embodiments, a higher order polynomial characterization may be applied to more accurately approximate the electrode's relationship between the electrode's strain and its resistivity.

The Controller

A controller can be in electrical communication with the actuator 120 and the sensor 140. The controller can be configured to adjust the application of the cuff's force on the urethra. The controller can receive a signal from the sensor corresponding to the pressure that the urethra is applying to the cuff 102. According to one embodiment, the controller can cause the actuator to cause the cuff to apply a first baseline pressure. The first baseline pressure can prevent urine flow through the urethra Optionally, the controller (e.g., microcontroller) can be a Texas Instruments CC26402RF microcontroller, which integrates a Bluetooth Low Energy (BLE) transceiver with an ultra-low-power microcontroller and analog-to-digital convertor to measure DET signals. Optionally, the circuitry of the SAUS device can be custom designed; however, it is also contemplated that the SAUS circuitry can be built from commercial off-the-shelf components. The SAUS device can include control software running on the microcontroller.

The SAUS device can also monitor a BLE radio for requests from a patient/user to release cuff pressure. This functional mode can permit normal voiding as in a healthy person by gradually removing cuff pressure after receiving a wireless void command. Many commercial microcontrollers now contain integrated BLE radios, including the CC26402RF microcontroller disclosed herein. Because voiding is an infrequent event, the SAUS device can reduce power usage of the BLE radio by only "listening" for a void command once every 10 seconds. A small, handheld remote control similar in size to a standard wireless key fob can be used to transmit void commands to the SAUS device.

Figure 5:
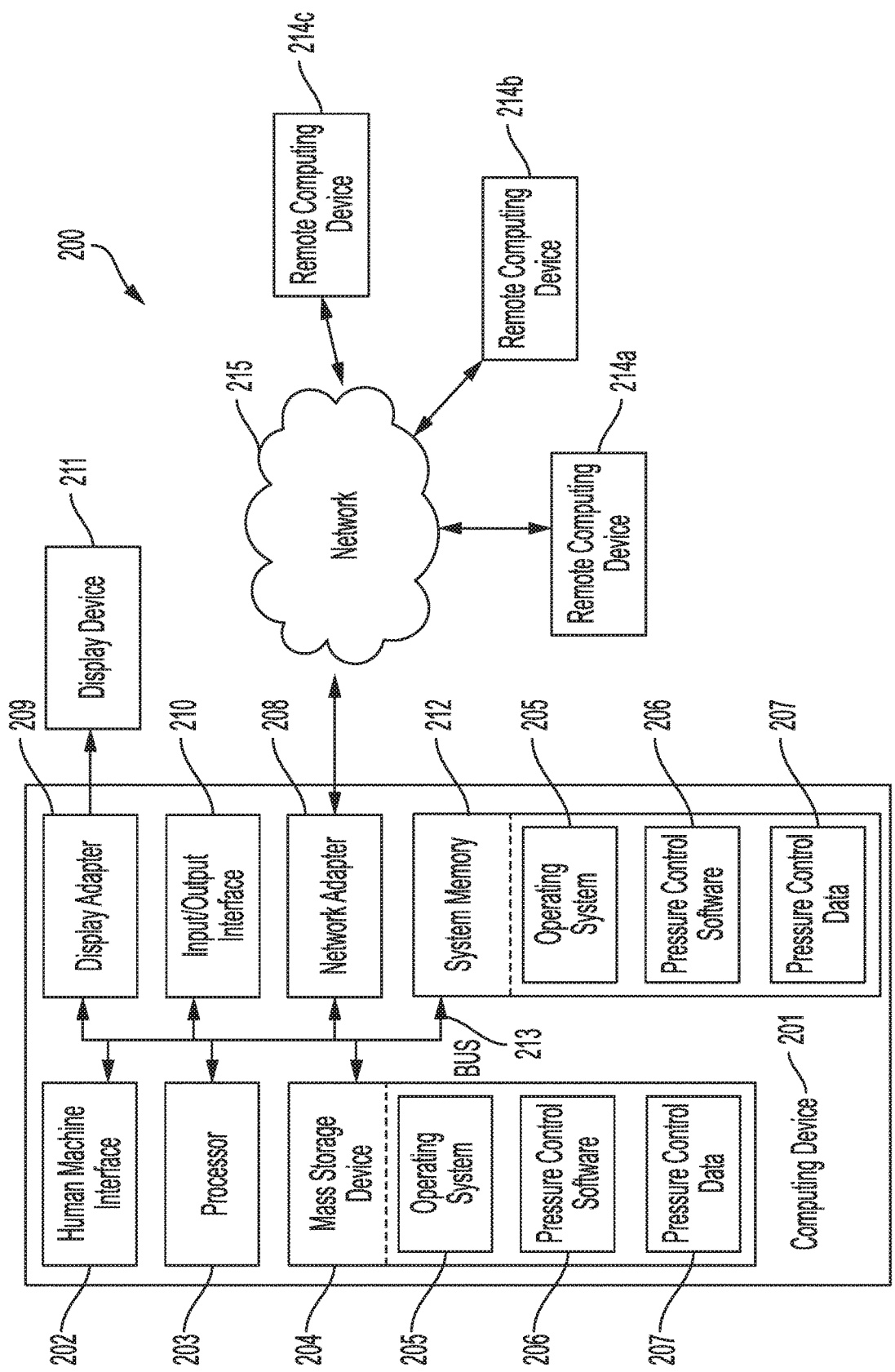
FIG. 5 is an exemplary computing system that can be used with SAUS device.

Although some embodiments of the SAUS device 100 refer to control via a microcontroller, it should be understood that various computing devices can be used to control aspects of the SAUS device 100. FIG. 5 shows an exemplary computing system 200 that can be used with SAUS device 100. Computing system 200 can include a computing device 201 and optionally a display 211 in electronic communication with the computing device. Alternatively, it is contemplated that the display 211 can be provided as a separate component from the computing device 201.

The computing device 201 may comprise one or more processors 203, a system memory 212, and a bus 213 that couples various components of the computing device 201 including the one or more processors 203 to the system memory 212. In the case of multiple processors 203, the computing device 201 may utilize parallel computing.

The bus 213 may comprise one or more of several possible types of bus structures, such as a memory bus, memory controller, a peripheral bus, an accelerated graphics port, and a processor or local bus using any of a variety of bus architectures.

The computing device 201 may operate on and/or comprise a variety of computer readable media (e.g., non-transitory). Computer readable media may be any available media that is accessible by the computing device 201 and comprises, non-transitory, volatile and/or non-volatile media, removable and non-removable media. The system memory 212 has computer readable media in the form of volatile memory, such as random access memory (RAM), and/or non-volatile memory, such as read only memory (ROM). The system memory 212 may store data such as pressure control data 207 and/or program modules such as operating system 205 and pressure control software 206 that are accessible to and/or are operated on by the one or more processors 203.

The computing device 201 may also comprise other removable/non-removable, volatile/non-volatile computer storage media. A mass storage device 204 may provide non-volatile storage of computer code, computer readable instructions, data structures, program modules, and other data for the computing device 201. The mass storage device 204 may be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Any number of program modules may be stored on the mass storage device 204. An operating system 205 and the pressure control software 206 may be stored on the mass storage device 204. One or more of the operating system 205 and the pressure control software 206 (or some combination thereof) may comprise program modules and the pressure control software 206. Pressure control data 207 may also be stored on the mass storage device 204. The pressure control data 207 may be stored in any of one or more databases known in the art. The databases may be centralized or distributed across multiple locations within the network 215.

Figure 2B:
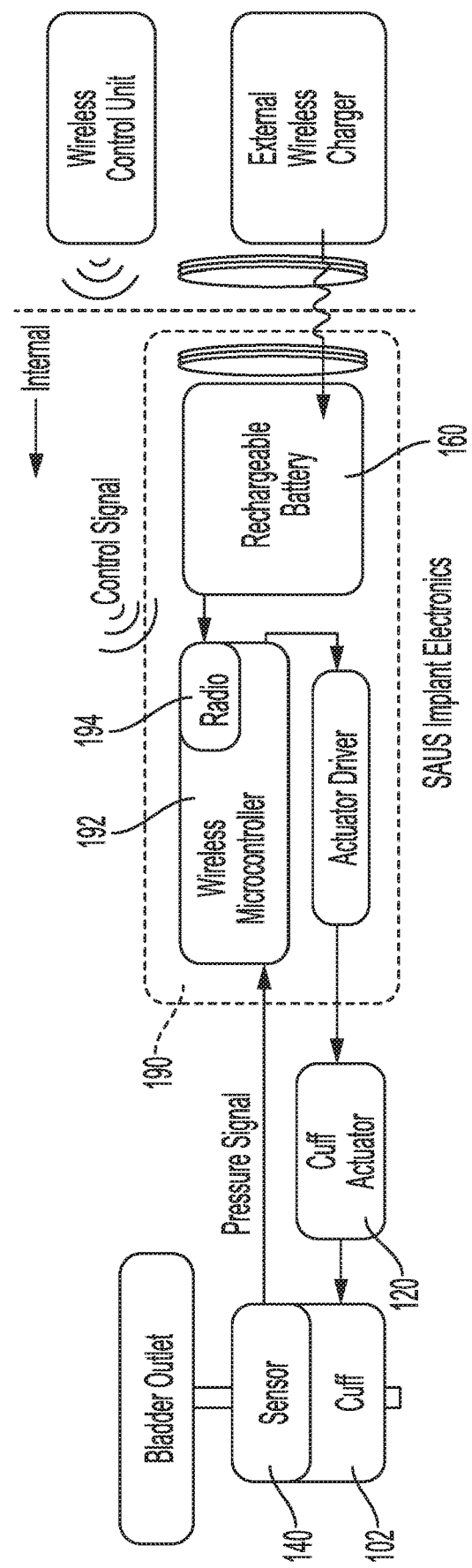

A patient may enter commands and information into the computing device 201 via an input device (e.g., the wireless control unit of FIG. 2B). Various other input devices may comprise, but are not limited to, a keyboard, a pointing device (e.g., a computer mouse, remote control), a microphone, a joystick, a scanner, tactile input devices such as gloves, and other body coverings, motion sensor, and the like. These and other input devices may be connected to the one or more processors 203 via a human machine interface 202 that is coupled to the bus 213, but may be connected by other interface and bus structures, such as a parallel port, game port, an IEEE 1394 Port (also known as a Firewire port), a serial port, network adapter 208, and/or a universal serial bus (USB).

The display device 211 may also be connected to the bus 213 via an interface, such as a display adapter 209. It is contemplated that the computing device 201 may have more than one display adapter 209 and the computing device 201 may have more than one display 211. A display 211 may be a monitor, an LCD (Liquid Crystal Display), light emitting diode (LED) display, television, smart lens, smart glass, and/or a projector. In addition to the display 211, other output peripheral devices may comprise components such as speakers (not shown) and a printer (not shown) which may be connected to the computing device 201 via Input/Output Interface 210. Any step and/or result of the methods may be output (or caused to be output) in any form to an output device. Such output may be any form of visual representation, including, but not limited to, textual, graphical, animation, audio, tactile, and the like. The display 211 and computing device 201 may be part of one device, or separate devices.

The computing device 201 may operate in a networked environment using logical connections to one or more remote computing devices 214a,b,c. A remote computing device 214a,b,c may be a personal computer, computing station (e.g., workstation), portable computer (e.g., laptop, mobile phone, tablet device), smart device (e.g., smartphone, smart watch, activity tracker, smart apparel, smart accessory), security and/or monitoring device, a server, a router, a network computer, a peer device, edge device or other common network node, and so on. Logical connections between the computing device 201 and a remote computing device 214a,b,c may be made via a network 215, such as a local area network (LAN) and/or a general wide area network (WAN). Such network connections may be through a network adapter 208. A network adapter 208 may be implemented in both wired and wireless environments. Such networking environments are conventional and commonplace in dwellings, offices, enterprise-wide computer networks, intranets, and the Internet. In further exemplary aspects, it is contemplated that the computing device 201 can be in communication with the remote computing devices 214a,b,c, e.g., through a Cloud-based network.

Application programs and other executable program components such as the operating system 205 are shown herein as discrete blocks, although it is recognized that such programs and components may reside at various times in different storage components of the computing device 201, and are executed by the one or more processors 203 of the computing device 201. An implementation of the pressure control software 206 may be stored on or sent across some form of computer readable media. Any of the disclosed methods may be performed by processor-executable instructions embodied on computer readable media.

Experimental Examples

It is contemplated that the disclosed implantable SAUS device can demonstrate its effectiveness by three exemplary performance metrics (Table 2). In particular, it is contemplated that the SAUS device 100 can have a smart sensing urethral cuff that is subjected to ten variable pressure tests, with at least eight of the ten tests showing a correlation between a pressure change and a response signal (Metric 1). It is further contemplated that the SAUS device can have a urethral cuff actuator/control system that is subjected to a series of 10 induced pressures and cuff release requests, with the cuff actuator/control system having a response time of less than 0.05 seconds for at least 8 of the 10 induced pressures (Metric 2). It is further contemplated that, following integration of the urethral cuff and the cuff actuator/control system, the SAUS device can be subjected to 10 dynamic variable pressure tests, with occlusivity being achieved in at least 8 of the 10 tests (Metric 3).

TABLE 2

Evaluation Metrics

| | Test | Description of Metric |
| --- | --- | --- |
| Metric 1 (Testing of Smart Sensing Urethral Cuff) | 10 variable pressure tests on cuff | 8/10 show correlation between pressure change and response signal |
| Metric 2 (Urethral Cuff Actuator System and Control: Test control methods for two modes of operation of the SAUS with response times of less than 0.05 seconds) | Measure time from response to control action for a series of 10 induced pressures and cuff release requests | Response time <0.05 seconds in 8/10 tests |
| Metric 3 (Validation of Integration of SAUS cuff and actuator/control systems) | 10 dynamic variable pressure tests with SAUS device | Occlusivity achieved in 8/10 tests |

Metric 1: Smart Sensing Urethral Cuff

It is contemplated that the smart sensing urethral cuff can provide near-uniform resting pressure on the urethra and sense pressure changes that require a pressure increase response from the SAUS actuator. This can allow the SAUS device to apply a lower resting cuff pressure to the urethra (decreasing atrophy/erosion, infection and resurgence of incontinence rates) that alternative devices while applying high cuff pressures to prevent leakages due to coughing, sneezing, positional changes, and the like. Dielectric elastomer transducers (DETs) that can serve as capacitive sensors are available from the University of Basel.

Figure 3:
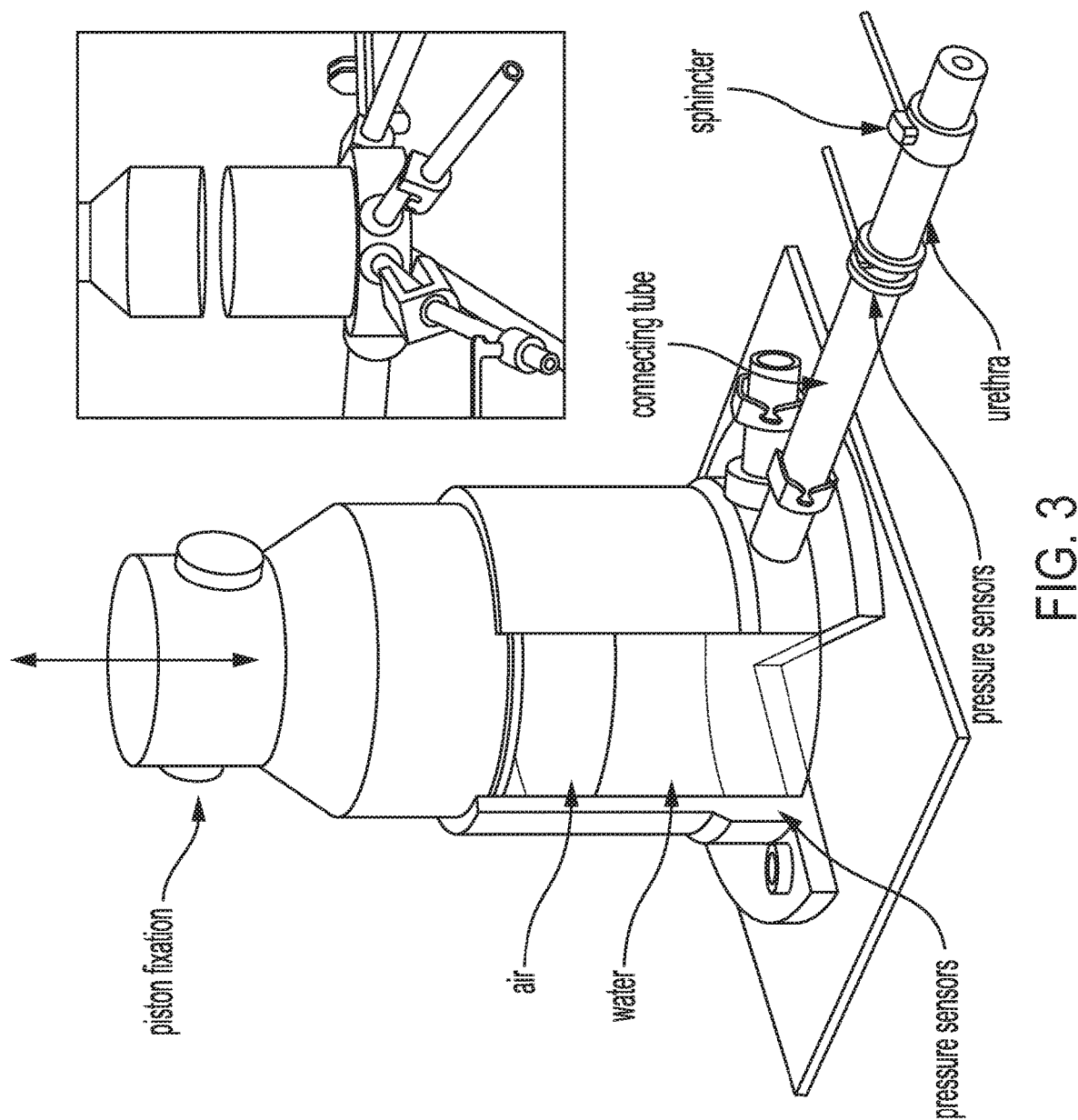
FIG. 3 depicts a modified TA INSTRUMENTS/BOSE ELECTROFORCE machine for variable pressure experiments as disclosed herein.

The DET sensor array can be attached to a silicon cuff over the entire 20 mm×25-35 mm cuff surface. The DET-sensor array can have a density of 0.1 sensors per mm$^2$ to the actual geometry of the SAUS cuff implant. Electrical contacts and the design of the DET sensor can rely on nanostructured interfaces and stretchable electronic interconnects, which can follow pressure-induced deformations of the SAUS cuff. Electrical and mechanical characterization of the integrated DET-sensor urethral cuff can be performed and can include stress-strain behavior, sensing sensitivity, leakage currents, and reliability under working conditions. Variable pressure experiments can be run on the smart urethral cuff to test correlation between the response signal observed from the cuff and the induced pressure. The cuff can be mounted around a cadaveric porcine urethra connected to a TA INSTRUMENTS/BOSE ELECTROFORCE test machine with tunable load profiles having a millisecond-resolution and adapt the internal fluid pressure within the urethra. (FIG. 3). One execution of the experiment can induce 10 pressures different from the established baseline (resting urethral pressure).

Metric 2: Urethral Cuff Actuator/Actuator Control

A primary function of the SAUS device can be to dynamically adjust cuff occlusion pressure to prevent leakage. However, the disclosed system can also allow triggered release of urine to protect the patient (bladder dangerously full) or on demand (user desire to void normally or medical intervention such as catheterization needed).

Figure 4:
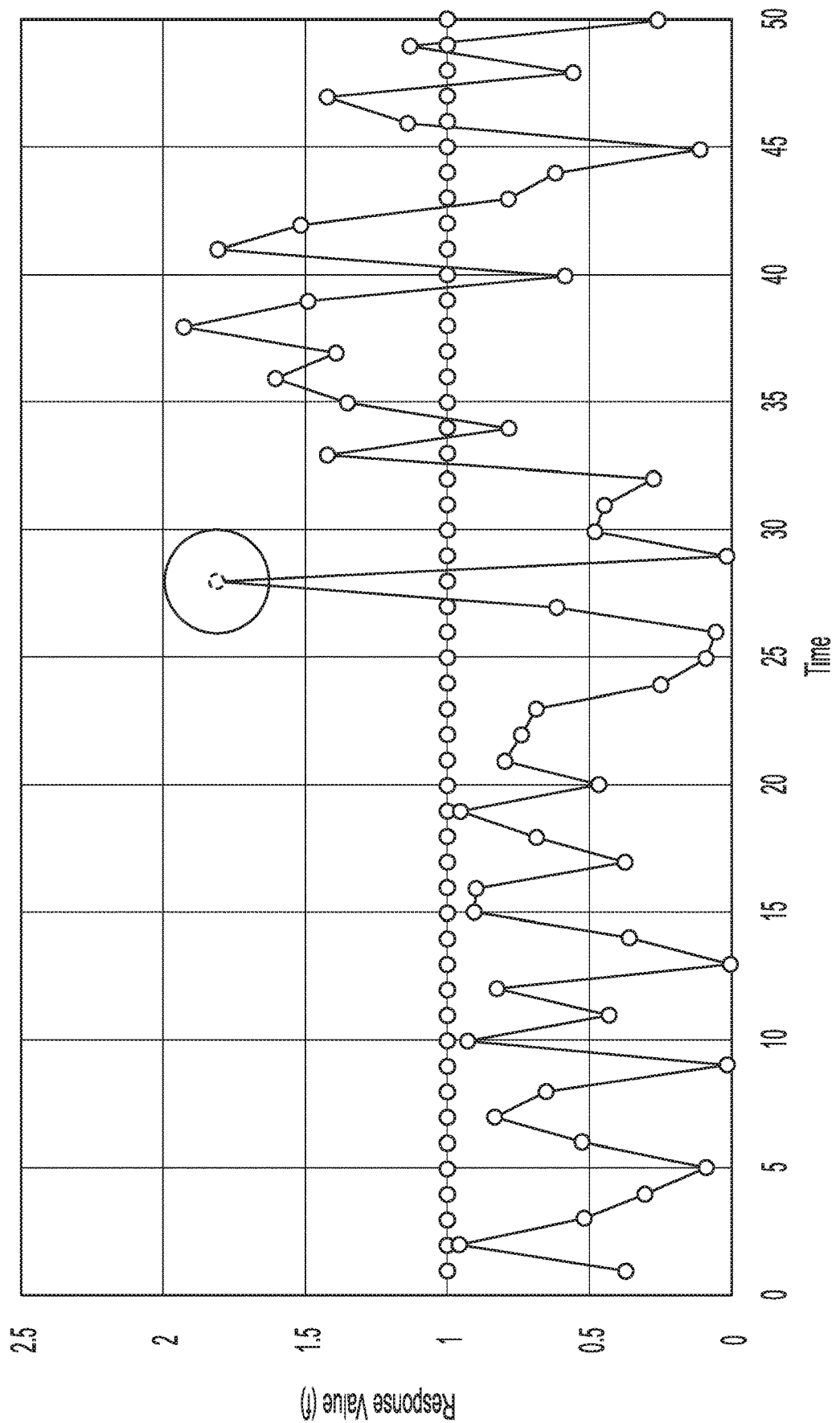
FIG. 4 is an exemplary DET response that exceeds a specified percentile (e.g., $99^{th}$ percentile) of a normal response, thereby actuating cuff closure.

The SAUS device can also provide control of cuff pressure during different phases of bladder function: urine storage and urine elimination. During urine storage, the SAUS control system can automatically vary the cuff pressure based on detected urethral pressures to eliminate leakage. Cuff pressure can be varied at either a baseline physiologic holding pressure or at a close pressure to simulate the sphincter pressure during guarding reflex in a healthy individual. It is contemplated that the SAUS device can implement a threshold limit decision system in which DET sensor signals exceeding the threshold can initiate the close pressure, and DET sensor signals below the threshold can keep a predetermined hold pressure. An example DET sensor response is shown in FIG. 4, where the time interval from 0-25 s represents a baseline DET response, and a $99^{th}$ percentile threshold is shown as a dashed line. For t>25 s, a urine leakage episode is simulated, with a sudden jump in the DET response. In this simple control scheme, when DET values exceed the $99^{th}$ percentile, instant cuff closure can be actuated to prevent urine leakage.

To support bench-test validation under variable pressure conditions, a SAUS development system can be fabricated. This system can integrate the wireless microcontroller, battery, and actuator onto a single printed circuit board for wired connection to DET sensors. A wireless charging coil can be integrated into the printed circuit board at the same scale as in an implanted device. The development system can be used to optimize the SAUS control software and to confirm DET measurement accuracy and power consumption. Wireless charging distance and efficiency, as well as wireless reception of void commands can also be tested on the development system. This development system can be used as an initial bench test prototype in determining compliance with Metric 3.

It is contemplated that all electronic components can be integrated into a wireless microsystem. The microsystem housing can be designed to ensure surgical efficacy during implantation and device removal (if necessary, e.g. due to complications). The bench test actuator system can be packaged for integration into an implantable and biocompatible SAUS device. Optionally, the packaging methods can be sufficient for SAUS testing in vitro (e.g. immersed in saline) but not qualified for preclinical use or testing in humans. The disclosed encapsulation, however, can permit full-scale testing of the SAUS device suitable for commercial demonstration and future translation.

Experimental Design & Methods: The open and closure time of the SAUS actuator and control system can be measured. For each operation mode (user request to release the cuff and sensor response exceeding the threshold), ten rapid requests to open or close the cuff for both control modes can be initiated. Sets of ten requests can be repeated, the response time and the correct action (void/increase cuff pressure) can be recorded.

Data Analysis & Interpretation: The ability of the SAUS device to respond to a control request and the time to execute the change in cuff pressure to void can be primary measurement aspects. Success can be measured by the number of times the actuator can respond in less than 30 ms. Reliably achieving 8 of 10 requests in less than 30 ms can be considered acceptable.

It is contemplated that the thermal noise floor for the SAUS device can be determined through spectral analysis. DET bandwidth can be limited to reduce random noise as far as possible without slowing sensor response. If the DET signal noise is still too great to identify a $99^{th}$ percentile threshold based on roiling variance calculation, increasingly more complex signal processing approaches can be used. These include the use of variable window length filters, or multi-resolution analysis such as wavelet transform. These methods have been previously used to produce time-varying thresholds in the analysis of bladder detrusor pressure waveforms. It is contemplated that mitigation of DET sensor baseline drift can be achieved using a discrete-time feedback circuit as is known in the art. Ultimately, false positives in detection are not detrimental to the health of the patient for the SAUS, so thresholds can be conservatively selected.

Too much latency in actuation, however, can impact the ability of SAUS to restore continence. Therefore, a 2× safety factor can be designed into the engineering constraints of actuator speed and computation time. If sufficient actuation speed cannot be achieved, it is contemplated that alternative control methods, such as proportional control, which have relaxed closed-loop time constraints, can be used.

When fully assembled, it is contemplated that the SAUS microsystem can integrate a wireless microcontroller, custom control software, and a cuff actuator as disclosed herein. Such a system can be suitable for benchtop characterization with DET sensors in accordance with Metric 3. Exemplary performance parameters for the SAUS actuator electronics are summarized in Table 3.

TABLE 3

Exemplary performance specifications for the SAUS actuator/microcontroller systems

| | |
|---|---|
| Control unit, weight | <10 g |
| Control unit size | 6 mm × 25 mm × 3 mm |
| DET measurement rate | 1000 samples/sec |
| DET measurement error | <1% full-scale |
| Automatic closure latency | <30 ms |
| Closing threshold false positive rate | <10% |
| Resting hold pressure | 50-70 mmHg |
| Closure pressure | 200 mmHg |
| Wireless empty command latency | <30 sec |
| Wireless charging distance | 20 mm |
| Battery lifespan per charge (estimated) | 5 days |

Metric 3: SAUS Device System Testing

It is contemplated that the SAUS cuff and actuator/control can be tested in a physiological phantom of stress urinary incontinence. The SAUS device can be evaluated on its ability to sense pressure changes on the urethra and respond with a suitable increase in cuff pressure, and its ability to release cuff pressure by wireless control. To achieve this objective, the wireless receiver system can communicate with the SAUS microcontroller, and the smart cuff sensor can interface seamlessly with the SAUS microcontroller.

The disclosed SAUS device can require cuff and actuator/control system integration. This can require demonstration that the SAUS actuator and controller can interface with and react to the smart urethral cuff.

Experimental Design and Methods: In Metric 3, the actuator and control system analyzed under Metric 2 can be attached to the smart urethral cuff analyzed under Metric 1. Static and variable pressure experiments can be run on the SAUS device. Static pressure experiments can apply a constant internal fluid pressure within a cadaveric porcine urethra to mimic the anatomy of human urethra. The response from the mounted SAUS device can be observed and recorded for the static pressure to verify readiness for variable pressure experiments. Static pressures experiments can apply a constant pressure and compare measured DET values with the built-in pressure sensors (26PC0250G6A Sortechnics, Germany) platform working at ranges of 0-200 mmHg on the TA INSTRUMENTS/BOSE ELECTROFORCE mechanical testing platform (FIG. 3). In variable pressure experiments, the SAUS device can be mounted around a cadaveric porcine urethra connected to a modified TA INSTRUMENTS/BOSE ELECTROFORCE mechanical testing platform. This can provide a user-defined pressure profile to the sample and simulate stress incontinence or abdominal events such as coughing. Testing of dynamic pressure loads (ramp, step or individual profiles) corresponding to cough profiles on a dynamic TA INSTRUMENTS/BOSE ELECTROFORCE mechanical testing platform can be performed. In addition, the viscoelastic response of the used urethra can be measured, the viscoelastic response can be compared with the DET measured values, and the response time of the SAUS device can be extracted. One execution of the experiment can induce 10 variable pressures, including ramp and step profiles. In Metric 3, the effectiveness of the SAUS device as a smart urethral cuff and actuator/control system can be determined by occlusivity and response time to increase or decrease cuff pressure.

Data Analysis & Interpretation: Metric 3 experiments focus on viscoelastic urethra response, response time, and occlusivity measurements. Response time can be measured in milliseconds (ms) and can be defined as the time from which a variable pressure is induced to the time that occlusivity is achieved. Occlusivity is the ability of the SAUS device to stop urine flow. The measure of occlusivity is the volume of leakage observed during experimentation and can be measured as a binary variable; leakage observed or leakage not observed. Response time of less than 50 ms and occlusivity (i.e. no leakage) in 8/10 tests can be evaluated as a successful SAUS demonstration. Remote control voiding can be evaluated on the cuff successfully releasing or increasing cuff pressure from a user control in 8/10 tests.

If occlusivity is not achieved, an alternative actuator that can apply greater force can be installed. If the response time is greater than 50 ms, the observed response time can first be evaluated for patient perceived effectiveness. If the observed response time is much greater than the ideal patient perceived response time, a detailed time study of the steps from cuff response measurement to actuator control request can be performed to identify which steps require improvement. A pitfall of the wireless cuff void activation is user misplacement of the remote or low battery in the remote. In these cases, patient void can be a result of emergency control responses identified in Metric 2.

Although several embodiments of the disclosure have been disclosed in the foregoing specification, it is understood by those skilled in the art that many modifications and other embodiments of the disclosure will come to mind one of ordinary skill in the art to which the disclosure pertains, having the benefit of the teaching presented in the foregoing description and associated drawings. It is thus understood that the disclosure is not limited to the specific embodiments disclosed herein, and that many modifications and other embodiments are intended to be included within the scope of the appended claims. Moreover, although specific terms are employed herein, as well as in the claims which follow, they are used only in a generic and descriptive sense, and not for the purposes of limiting the disclosure, nor the claims which follow.

EXEMPLARY ASPECTS

In view of the described products, systems, and methods and variations thereof, herein below are described certain more particularly described aspects of the invention. These particularly recited aspects should not however be interpreted to have any limiting effect on any different claims containing different or more general teachings described herein, or that the "particular" aspects are somehow limited in some way other than the inherent meanings of the language literally used therein.

Aspect 1: An artificial urinary sphincter comprising: a cuff configured to surround a portion of a length of a urethra; an actuator in communication with the cuff and configured to selectively apply a force to the cuff to thereby apply a variable amount of pressure to the urethra; a controller in electrical communication with the actuator and configured to adjust the application of the force by the actuator to cause the cuff to apply the variable amount of pressure to the urethra; and at least one sensor in communication with the controller, wherein the sensor is configured to detect pressure applied against the cuff by the urethra, wherein the controller is configured to cause the cuff to apply a first closing pressure to the urethra; wherein, in response to a detection of a threshold pressure increase by the sensor, the controller is configured to cause the cuff to apply a second closing pressure that is greater than the first closing pressure and that prevents urine from exiting the urethra.

Aspect 2: The artificial urinary sphincter of aspect 1, wherein the at least one sensor is a dielectric elastomer transducer.

Aspect 3: The artificial urinary sphincter of aspect 2, wherein the at least one sensor comprises a plurality of metal electrodes embedded in an elastic elastomer membrane.

Aspect 4: The artificial urinary sphincter of aspect 2 or aspect 3, wherein the at least one sensor has a response time below 20 milliseconds in response to pressure changes.

Aspect 5: The artificial urinary sphincter of any one of aspects 2-4, wherein the at least one sensor is configured to change capacitance in response to mechanical deformation, and wherein the controller is configured to detect a change in capacitance to the sensor.

Aspect 6: The artificial urinary sphincter of any one of the preceding aspects, wherein the actuator is configured to move the cuff from an open position to a closed position.

Aspect 7: The artificial urinary sphincter of any one of the preceding aspects, wherein at least a portion of the artificial urinary sphincter is configured to be installed in a pelvic cavity of a user.

Aspect 8: The artificial urinary sphincter of any one of the preceding aspects, wherein the actuator is an electric actuator.

Aspect 9: The artificial urinary sphincter of aspect 8, wherein the actuator is a linear actuator.

Aspect 10: The artificial urinary sphincter of any one of the preceding aspects, wherein, upon a detected condition, the controller is configured to cause the actuator reduce the pressure to the cuff to thereby move the actuator to the open position.

Aspect 11: The artificial urinary sphincter of aspect 10, further comprising a wireless receiver in communication with the controller, wherein the wireless receiver is configured to receive a release signal, wherein the detected condition is a receipt of the release signal.

Aspect 12: The artificial urinary sphincter of aspect 10, wherein the detected condition is a sensed pressure from the at least one sensor that is greater than a threshold value and that is maintained for a threshold amount of time.

Aspect 13: The artificial urinary sphincter of aspect 1, wherein the artificial urinary sphincter comprises a battery that is configured to be charged wirelessly.

Aspect 14: The artificial urinary sphincter of aspect 13, wherein the artificial urinary sphincter comprises a charge receiver that is configured to be implanted between 2 and 3 cm below the skin of a user.

Aspect 15: The artificial urinary sphincter of any of the preceding aspects, wherein the first closing pressure is between 50 and 70 mmHg.

Aspect 16: The artificial urinary sphincter of any of the preceding aspects, wherein the second closing pressure is about 200 mmHg.

Aspect 17: A method comprising:
  implanting the artificial urinary sphincter as in any of aspects 1-16 in a patient;
  detecting, using the sensor, a pressure measurement above the threshold pressure; and
  in response to receiving the pressure measurement above the threshold pressure, providing a signal to the actuator to cause the cuff to apply the second closing pressure.

What is claimed is:

1. An artificial urinary sphincter comprising:
  a cuff configured to surround a portion of a length of a urethra, the cuff comprising a housing and a band that is retractable into and protractable from the housing;
  an actuator in communication with the cuff and configured to selectively apply a force to the cuff to thereby apply a variable amount of pressure to the urethra, wherein the actuator is an electric linear actuator that is configured to retract and protract the band relative to the housing;
  a controller in electrical communication with the actuator and configured to adjust the application of the force by the actuator to cause the cuff to apply the variable amount of pressure to the urethra; and
  at least one sensor integrated into or coupled to the cuff, wherein the at least one sensor is in communication with the controller, wherein the at least one sensor is configured to detect pressure applied against the cuff by the urethra, wherein the at least one sensor comprises an array of dielectric elastomer transducers, wherein the array of dielectric elastomer transducers comprises a plurality of metal electrodes embedded in an elastic elastomer membrane,
  wherein the controller is configured to cause the cuff to apply a first closing pressure to the urethral, and
  wherein, in response to a detection of a threshold pressure increase by the sensor, the controller is configured to cause the cuff to apply a second closing pressure that is greater than the first closing pressure and that prevents urine from exiting the urethra.

2. The artificial urinary sphincter of claim 1, wherein the at least one sensor has a response time below 20 milliseconds in response to pressure changes.

3. The artificial urinary sphincter of claim 1, wherein the at least one sensor is configured to change capacitance in response to mechanical deformation, and wherein the controller is configured to detect a change in capacitance to the sensor.

4. The artificial urinary sphincter of claim 1, wherein the actuator is configured to move the cuff from an open position to a closed position.

5. The artificial urinary sphincter of claim 4, wherein, upon a detected condition, the controller is configured to cause the actuator reduce the pressure to the cuff to thereby move the cuff to the open position.

6. The artificial urinary sphincter of claim 5, further comprising a wireless receiver in communication with the controller, wherein the wireless receiver is configured to receive a release signal, wherein the detected condition is a receipt of the release signal.

7. The artificial urinary sphincter of claim 5, wherein the detected condition is a sensed pressure from the at least one sensor that is greater than a threshold value and that is maintained for a threshold amount of time.

8. The artificial urinary sphincter of claim 1, wherein at least a portion of the artificial urinary sphincter is configured to be installed in a pelvic cavity of a user.

9. The artificial urinary sphincter of claim 1, wherein the artificial urinary sphincter comprises a battery that is configured to be charged wirelessly.

10. The artificial urinary sphincter of claim 9, wherein the artificial urinary sphincter comprises a charge receiver that is configured to be implanted between 2 and 3 cm below the skin of a user.

11. The artificial urinary sphincter of claim 1, wherein the first closing pressure is between 50 and 70 mmHg.

12. The artificial urinary sphincter of claim 1, wherein the second closing pressure is about 200 mmHg.

13. The artificial urinary sphincter of claim 1, wherein the housing comprises a Y-shaped body having an interior path through which the band extends.

14. The artificial urinary sphincter of claim 13, wherein the Y-shaped body cooperates with the band to define a portion of the cuff that is configured to engage the urethra.

15. A method comprising:
  implanting an artificial urinary sphincter in a patient, the artificial urinary sphincter comprising:
    a cuff configured to surround a portion of a length of a urethra of the patient, the cuff comprising a housing and a band that is retractable into and protractable from the housing;
    an actuator in communication with the cuff and configured to selectively apply a force to the cuff to thereby apply a variable amount of pressure to the urethra, wherein the actuator is an electric linear actuator that is configured to retract and protract the band relative to the housing;

a controller in electrical communication with the actuator and configured to adjust the application of the force by the actuator to cause the cuff to apply the variable amount of pressure to the urethra; and at least one sensor integrated into or coupled to the cuff, wherein the at least one sensor is in communication with the controller, wherein the at least one sensor is configured to detect pressure applied against the cuff by the urethra, wherein the at least one sensor comprises an array of dielectric elastomer transducers, wherein the array of dielectric elastomer transducers comprises a plurality of metal electrodes embedded in an elastic elastomer membrane;

detecting, using the sensor, a pressure measurement above a threshold pressure; and in response to receiving the pressure measurement above the threshold pressure, providing a signal to the actuator to cause the cuff to apply a second closing pressure that is greater than the first closing pressure and that prevents urine from exiting the urethra.

16. The method of claim 15, wherein the at least one sensor changes capacitance in response to mechanical deformation, and wherein the controller detects a change in capacitance to the sensor.

17. The method of claim 15, wherein, upon a detected condition, the controller causes the actuator reduce the pressure to the cuff to thereby move the cuff to an open position.

* * * * *